United States Patent [19]

Jones et al.

[11] 4,255,358

[45] Mar. 10, 1981

[54] PROCESS FOR THE PRODUCTION OF HEXANITROSTILBENE

[75] Inventors: Ronald H. Jones, London; Alexander W. H. Pryde, Waltham Abbey, both of England

[73] Assignee: The Secretary of State for Defence in Her Britannic Majesty's Government of the United Kingdom of Great Britain and Northern Ireland, London, England

[21] Appl. No.: 17,973

[22] Filed: Mar. 6, 1979

[30] Foreign Application Priority Data

Mar. 13, 1978 [GB] United Kingdom ............... 9909/78

[51] Int. Cl.³ .................. C07C 76/02; C07C 79/10
[52] U.S. Cl. ........................ 568/931; 149/105; 149/111
[58] Field of Search ............... 260/645; 149/105, 111

[56] References Cited

U.S. PATENT DOCUMENTS

| | | | |
|---|---|---|---|
| 3,505,413 | 4/1970 | Shipp | 260/645 |
| 3,699,176 | 10/1972 | Syrop | 260/645 |
| 4,085,152 | 4/1978 | Salter | 260/645 |

*Primary Examiner*—Deborah L. Kyle

*Attorney, Agent, or Firm*—Stevens, Davis, Miller & Mosher

[57] ABSTRACT

A process for the production of 2, 2', 4, 4', 6, 6'-hexanitrostilbene, which gives a readily isolable product and in which solvent recovery is relatively straightforward, is described.

An alkali or alkaline earth hypochlorite was reacted with 2, 4, 6-trinitrotoluene in an aqueous organic solvent, preferably containing tetrahydrofuran. The reactant mixture was allowed to stand for at least 30 minutes when a solution of a mineral acid, especially sulphuric acid, was added, with stirring, to acidify the mixture to a final pH of less than 5, preferably between 0.5 and 1.0, especially 0.7. This acidification caused agglomeration of the hexanitrostilbene. When complete mixing of the solutions had been obtained, the stirring was stopped and the mixture allowed to settle and separate into two layers. The top layer, which contained little solid product, was run off through a filter and the filtrate was treated separately to recover solvents, especially tetrahydrofuran. The bottom layer, which contained most of the solid product, was then passed through the filter to collect the agglomerated solid.

Washing the product afforded hexanitrostilbene that has a surface area of between 3 and 6 meter² gm⁻¹ when measured by gas adsorption techniques.

12 Claims, 1 Drawing Figure

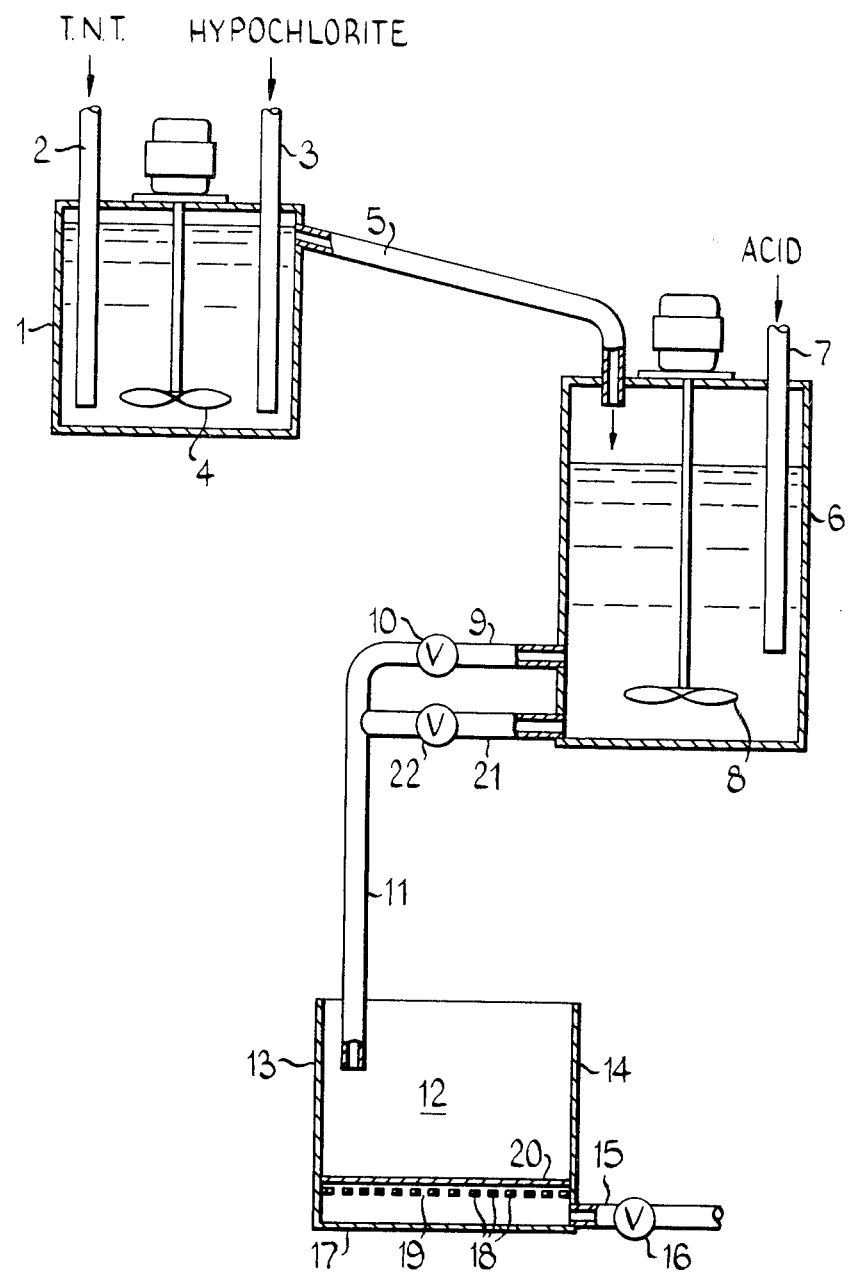

PROCESS FOR THE PRODUCTION OF HEXANITROSTILBENE

The present invention relates to the production of 2,2',4, 4', 6, 6'-hexanitrostilbene.

2, 2', 4, 4', 6, 6'-hexanitrostilbene (HNS) has been used as an explosive, but is especially useful as a crystal-modifying additive in melt-cast trinitrotoluene (TNT) charges.

A preparation of hexanitrostilbene is described in U.S. Pat. No. 3,505,413. This involves reaction of sodium hypochlorite with 2, 4, 6-trinitrotoluene (TNT) at 15° C. in a tetrahydrofuran/methanol solvent. The product is obtained as a fine suspension which is difficult to filter and after acetone washing to remove co-precipitated impurities, yields are about 30 to 35% of the theoretical weight of HNS. In addition to the crude HNS large amounts of so-called "red oil" are also produced and the presence of this material greatly complicates the separation of the product and the reuse of the tetrahydrofuran solvent. It has been reported that the yield of HNS may be increased to about 50% by addition of an amine (U.K. Pat. No. 1,513,221) or by pH control (U.K. Pat. Appln 9077/78) after the initial mixing of TNT and hypochlorite. However the product is still difficult to separate and the "red oil", although somewhat reduced, still greatly complicates the separation and solvent recovery procedures rendering the process very expensive to scale-up.

There is therefore an outstanding need for a process for producing hexanitrostilbene, which will give a readily isolable product and in which solvent recovery is relatively straight-forward and hence inexpensive to carry out.

According to the present invention there is provided a process for the preparation of 2, 2', 4, 4', 6, 6'-hexanitrostilbene which comprises the steps of:

(a) reacting an alkali or alkaline earth metal hypochlorite with 2, 4, 6-trinitrotoluene in an aqueous organic solvent;

(b) allowing said reactant mixture to stand for a period of at least 30 minutes;

(c) after said standing period, adding a solution of a mineral acid with stirring, to said reactant mixture to acidify the mixture to a final pH of less than 5 so as to cause agglomeration of the hexanitrostilbene;

(d) allowing the mixture obtained in step (c) to settle and separate into two layers;

(e) passing at least the lower of said two layers through a filter to filter off the suspended product.

The product may then be washed by suitable solvents, especially acetone followed by water or aqueous acetone. In the settlement stage, the liquid forms two layers, the lower of which contains substantially all of the HNS and most of the red oil. The upper layer contains most of the organic solvent, together with some of the water, some inorganic salts and a small proportion of the impurities forming the red oil. Thus by this process separation of the solvent for the TNT from the HNS produced is readily achieved and the separated solvent layer can be sent on for recovery of the solvent while the HNS-containing layer can be subjected to procedures to extract the HNS product. In connection with the latter, a further advantage of the process of the invention arises in that provided the reaction mixture has not been stirred or agitated significantly during the standing period the acidification causes the fine HNS particles to agglomerate into aggregates which are more readily filtered than the original material. Thus provided care is taken to avoid breaking up these aggregates, the separation and purification of the HNS is also greatly simplified.

As in previously reported processes for preparing HNS from TNT and hypochlorites, the major proportion of the water content in the aqueous organic solvent will be provided by an aqueous solution of hypochlorite, although water may also be introduced with, for example, the organic component. Preferably the total water content is between 40 and 50% by weight. The organic component of the solvent may, for example, be dioxan, diglyme or acetonitrile or mixtures thereof, but is preferably a mixture of tetrahydrofuran with another solvent especially methanol.

Sodium hypochlorite is preferably used as the hypochlorite reagent and the solution preferably contains from 4 to 7% (w/v), most preferably 4.5% of available chloride. The reaction should preferably be conducted at a temperature in the range of $-5°$ to 25° C. throughout. A temperature of from 10° to 20° C. is especially preferred. Since the reaction is exothermic the reactor should be provided with cooling coils so that the desired temperature can be maintained.

Hydrochloric acid or preferably, sulphuric acid, may be used as the mineral acid since their salts do not generally cause any difficulties in the separation and purification of the HNS product. In the case of mineral acid salts which tend to precipitate out, these procedures might be complicated as a result.

The process may be carried out batch-wise or by a semi-continuous process wherein the hypochlorite and TNT solutions are simultaneously fed into the reactor at a rate which is most suitably chosen to allow the reactants a residence time in the reactor of from 1 to 3 minutes, before transferring the reactant mixture to a separate vessel for standing. The standing or ageing period is at least 30 minutes and should preferably be longer, eg on the order of two hours and possibly up to 12 hours. During this time the mixture preferably should not be stirred and does not need to be cooled.

After ageing, the mineral acid solution is added with mild stirring in order to ensure complete mixing of the solutions. The amount of acid added is such that the HNS is agglomerated to at least some extent and can be checked by observation of the mixture which lightens in colour from red to yellow. The pH of the mixture should be less than 5 at this stage, preferably less than 1, and particularly about 0.7. There is no benefit in taking the pH below 0.5 and generally of course it will be desirable to use the minimum amount of acid possible, consistent with a satisfactory separation of the mixture occurring and a good product being obtained.

An overall stirring period, during and after acidification, of about 15 minutes will generally be adequate to produce complete mixing of the solutions and is followed by a settling period of at least half an hour. During the settling period the mixture separates out into two layers. When the separation appears to be complete ie when no further change occurs, it is preferred first to run the top layer through a filter, followed by the bottom layer. The bottom layer contains the bulk of the product in suspension, but by passing both layers through the filter any product which may be in the upper layer will also be separated out on the filter. After passing through the filter the top layer may be collected separately and treated to recover the THF-containing solvent, for example by steam distillation.

The residue in the filter is preferably covered with a cloth and then displacement washed with acetone to remove "red oil" and other impurities, the filtrate optionally being collected for recovery of the acetone. After the acetone wash, the residue (product) is displacement washed with distilled or demineralized water until the effluent is free from salts derived from the mineral acid. The residue (product) can then be dried if required, conveniently by a first stage of pressing out excess water, followed by hot air drying.

2, 2', 4, 4', 6, 6'- Hexanitrostilbene produced by the process of this invention is an extremely fine powder having plate-like crystals and a surface area of 2 to 3 meter$^2$ gm$^{-1}$ when measured by air permeatry and 3–6 meter$^2$ gm$^{-1}$ when measured by gas absorption techniques. The pelleting properties of the NHS of this invention are good. For example a pressure of 45 lbs in$^{-2}$ acting on a 6 inch diameter piston which in turn acts on a 0.2 inch diameter spigot which presses onto the HNS sample produces HNS pellets of 95% theoretical maximum density, which are substantially stronger than pellets formed by HNS obtained by filtration from alkali.

A specific process according to the present invention will now be described by way of example only and with reference to the FIGURE which shows diagrammatically an embodiment of the present invention.

75 l of sodium hypochlorite solution containing 6.5% w/v available chlorine is run into a blowing egg (not shown) of 30 gallon (136.4 l) capacity made of enamelled cast iron. 8 Kg of TNT is dissolved in a wet THF/methanol mixed solvent comprising 68.5 l of tetrahydrofuran, 34.3 l of methanol and 4 l of water in a 30 gallon (136.4 l) stainless steel blowing egg. A heel of 2 l of a mixture of 40% water, 40% THF, and 20% methanol (by volume) is added to a 12 l stainless steel reactor (1) fitted with a cooling coil (not shown). The heel is brine cooled to 15° C. and then the TNT solution is fed into the reaction vessel (1) through supply pipe (2) whilst the hypochlorite solution is fed into the vessel (1) through second supply pipe (3). Equivalent rates of feeding the two solutions from their respective blowing eggs into the reaction vessel are obtained by controlling the pressure of air admitted into said respective blowing eggs. The hypochlorite feed is given a slight head. The feed liquids pass through filters (not shown) before entering the reactor (1) and the rates are observed in rotameters (not shown).

The reactor (1) is maintained at 15° C. and the feed rates at this temperature give a residence time in the reactor (1) of about 1.8 minutes. At this feed rate the feed materials are exhausted after about 25 minutes and the feeds are then turned off. During this period the reacted mixture flows continuously out of the reactor (1) through a transfer pipe (5) and into an ageing vessel (6) made of high density polyethylene. After exhaustion of the feeds the reactor is stirred for about another minute with stirrer 4 and is then emptied into the ageing vessel (6). The ageing vessel (6) has a capacity of 100 gallons (454.5 l ) and is fed with two consecutive batches from the reactor (1). After two hours standing in the ageing vessel (6), 40 liters of 50% sulphuric acid is added to said aging vessel (6) through third supply pipe (7). The reaction mixture is stirred, by stirrer (8), during the acid addition and then for a further 15 minutes.

After stirring, the mixture is allowed to settle for about 90 minutes and the top layer, which constitutes about ¾ of the total volume, is run off through an upper outlet pipe (9), fitted with a valve (10), along second transfer pipe (11) to a filter (12). The filter (12) consists of a specially adapted 50 gallon (227.2 l) high density polyethylene vessel (13). In one of the side walls (14) and near the bottom of the vessel is a run-off pipe (15) fitted with a valve (16). Whilst 6 inches (152 mm) above the vessel's base (17) is fitted a ½ inch (12.7 mm) thick polyethylene sheet (18) drilled with 90 holes (19) of ⅜ inch (9.52 mm) diameter, the sheet being strengthened by polyethylene ribs (not shown). The sheet (18) is covered with a cotton filter cloth (20).

After running the top layer through the filter (12) the bottom layer from the ageing vessel (6) is run out of said vessel (6), through a lower outlet pipe (21), fitted with a valve (22), along second transfer pipe (11) and into the filter (12). The bottom layer filters only rather slowly and is conveniently left to drain into a 30 gallon (136.4 l) enamelled cast iron receiver vessel (not shown) overnight. The filtrate is passed on for solvent recovery while a cloth (not shown) is placed on the filter cake (not shown) in the filter (12) and 80 l of recovered acetone sprayed on and allowed to perform a displacement wash. After this the filter cake is washed with 20 l of fresh acetone and after that, with 120 l of distilled or demineralized water. Percolation of the water is continued until the effluent is free from sulphate by barium chloride test (more than 120 l of water may be required for this purpose).

Following washing, the water-wet cake of HNS product is removed from the filter (12) to a cloth bag (not shown) and further water is removed by pressure. The HNS may be completely dried by hot air drying to give a yield of 5.5 Kg (35% of theoretical).

We claim:

1. In a process for preparing 2, 2', 4, 4', 6, 6' hexanitrostilbene wherein an alkali or alkaline earth metal hypochlorite and 2, 4, 6-trinitrotoluene are reacted in an aqueous organic solvent, and 2, 2', 4, 4', 6, 6' hexanitrostilbene is precipitated, the improvement which comprises
   (a) allowing the reaction mixture to stand for at least 30 minutes after the said reactants are mixed together,
   (b) mixing with the reaction mixture a mineral acid with stirring to adjust the pH to less than 5 and agglomerating the hexanitrostilbene precipitate,
   (c) allowing the product of (b) to separate into upper and lower layers, and
   (d) filtering the lower of said layers to remove the suspended product.

2. A process according to claim 1 wherein the solid product obtained by filtration is washed with acetone followed by water or aqueous acetone.

3. A process according to claim 1 wherein the reactant mixture is acidified to a pH between 0.5 and 1.0.

4. A process according to claim 3 wherein the reactant mixture is acidified to a pH of about 0.7.

5. A process according to claim 1 wherein the mineral acid is selected from sulphuric acid and hydrochloric acid.

6. A process according to claim 1 wherein the overall period of stirring during and after acidification is about 15 minutes.

7. A process according to claim 1 wherein the overall period of settling is at least 30 minutes.

8. A process according to claim 1 wherein the alkali or alkaline earth hypochlorite is added as a solution having a concentration of free chlorine within the range 4 to 7% (w/v).

9. A process according to claim 8 wherein the alkali or alkaline earth hypochlorite is added as a solution having a concentration of free chlorine of about 4.5% (w/v).

10. A process according to claim 1 wherein the alkali or alkaline earth hypochlorite comprises sodium hypochlorite.

11. A process according to claim 1 wherein the aqueous organic solvent contains tetrahydrofuran.

12. A process according to claim 1 wherein the aqueous organic solvent comprises tetrahydrofuran and methanol, in the ratio of about 2 to 1 (v/v), and water.

* * * * *